United States Patent
Shinohara

(10) Patent No.: US 9,617,105 B2
(45) Date of Patent: Apr. 11, 2017

(54) WRINKLE SMOOTHING METHOD FOR A COMPOSITE BODY OF A CONTINUOUS SHEET RELATED TO ABSORBENT ARTICLES

(75) Inventor: Akira Shinohara, Kanoji (JP)

(73) Assignee: UNICHARM CORPORATION, Ehime (JP)

(*) Notice: Subject to any disclaimer, the term of this patent is extended or adjusted under 35 U.S.C. 154(b) by 781 days.

(21) Appl. No.: 13/822,477

(22) PCT Filed: Sep. 27, 2011

(86) PCT No.: PCT/JP2011/071966
§ 371 (c)(1),
(2), (4) Date: Jun. 3, 2013

(87) PCT Pub. No.: WO2012/043517
PCT Pub. Date: Apr. 5, 2012

(65) Prior Publication Data
US 2013/0244855 A1 Sep. 19, 2013

(30) Foreign Application Priority Data
Sep. 30, 2010 (JP) .................................. 2010-222491

(51) Int. Cl.
*B65H 23/00* (2006.01)
*B65H 23/032* (2006.01)
(Continued)

(52) U.S. Cl.
CPC ....... *B65H 23/00* (2013.01); *A61F 13/15764* (2013.01); *B31F 7/00* (2013.01);
(Continued)

(58) Field of Classification Search
CPC .......... A61F 13/15585; A61F 13/15601; A61F 13/15661; A61F 13/15666; A61F 13/15674;
(Continued)

(56) References Cited

U.S. PATENT DOCUMENTS 5,046,272 A 9/1991 Vogt et al.
5,368,909 A * 11/1994 Langdon ................. A61F 13/15
428/131
(Continued)

FOREIGN PATENT DOCUMENTS

JP 2000014701 1/2000
JP 2000014701 A * 1/2000
(Continued)

OTHER PUBLICATIONS

EPO machine translation of JP3568146, retrieved Dec. 9, 2015, 7 pages.*
(Continued)

*Primary Examiner* — Stephen F Gerrity
*Assistant Examiner* — Joshua Kotis
(74) *Attorney, Agent, or Firm* — Hauptman Ham, LLP

(57) ABSTRACT

A wrinkle smoothing device for a composite body of a continuous sheet related to an absorbent article includes a first belt that moves along a first travel path while retaining the central portion of the continuous sheet, and second and third belts that move along second and third travel paths while retaining side portions of the continuous sheet. The second and third travel path are inclined from the first travel path such that a downstream side is more spaced apart from the first travel path than an upstream side. The second and third belts retain side portions of the continuous sheet while relatively sliding in the width direction of the continuous sheet.

8 Claims, 10 Drawing Sheets

(51) Int. Cl.
*B65H 20/10* (2006.01)
*B65H 23/02* (2006.01)
*A61F 13/15* (2006.01)
*B31F 7/00* (2006.01)

(52) U.S. Cl.
CPC ............ *B65H 20/10* (2013.01); *B65H 23/02* (2013.01); *B65H 23/0324* (2013.01)

(58) Field of Classification Search
CPC ...... A61F 13/15764; B65H 2404/1452; B65H 2404/255; B65H 59/24; B65H 59/30; B65H 20/10–20/12; B65H 23/00; B65H 23/02; B65H 23/022; B65H 23/025; B65H 23/0251–23/0258; B65H 23/032–23/038; B65H 23/10; B65H 2801/57; B31F 7/00
USPC .......... 198/689.1, 817, 861.6, 631.1, 457.03; 493/406, 418, 460, 465, 466, 467, 393, 493/379, 380–382; 26/51; 156/494–496, 156/229, 163, 164
See application file for complete search history.

(56) References Cited

U.S. PATENT DOCUMENTS

| | | | | |
|---|---|---|---|---|
| 5,547,531 A | * | 8/1996 | Allen | A44B 18/0011 156/163 |
| 5,693,165 A | * | 12/1997 | Schmitz | A61F 13/15764 156/163 |
| 5,795,344 A | * | 8/1998 | Chappell | A61F 13/533 604/379 |
| 5,932,497 A | * | 8/1999 | Morman | A61F 13/15731 264/41 |
| 6,000,531 A | * | 12/1999 | Martin | B65G 23/26 198/369.2 |
| 6,648,122 B1 | * | 11/2003 | Hirsch | B65G 47/848 156/552 |
| 6,938,309 B2 | * | 9/2005 | Gorman | B29C 55/08 26/51 |
| 7,618,513 B2 | * | 11/2009 | Meyer | A61F 13/15699 156/265 |
| 2009/0320663 A1 | | 12/2009 | Yamamoto | |
| 2010/0032263 A1 | | 2/2010 | Yamamoto | |
| 2010/0212136 A1 | * | 8/2010 | Hjalmarsson | B32B 37/0046 29/428 |

FOREIGN PATENT DOCUMENTS

JP 2010035932 2/2010
WO 8706189 A1 10/1987

OTHER PUBLICATIONS

Office Action dated Oct. 9, 2015, corresponding to European Patent Application No. 11829070.9.
PCT/JP2011/071966 International Search Report dated Nov. 15, 2011.
Office Action issued May 22, 2014, corresponds to Chinese patent application No. 201180047119.9.
Extended European Search Report dated Aug. 5, 2014, corresponds to European patent application No. 11829070.9.

* cited by examiner

B-B VIEW

C-C VIEW

B-B VIEW

C-C VIEW

WRINKLE SMOOTHING METHOD FOR A COMPOSITE BODY OF A CONTINUOUS SHEET RELATED TO ABSORBENT ARTICLES

RELATED APPLICATIONS

The present application is a National Phase of PCT/JP2011/071966, filed Sep. 27, 2011, and is based on, and claims priority from, Japanese Application No. 2010-222491, filed Sep. 30, 2010.

TECHNICAL FIELD

The present invention relates to a wrinkle smoothing device and a wrinkle smoothing method of a composite body of a continuous sheet for absorbent articles involved in manufacturing absorbent articles such as disposable diapers and the like.

BACKGROUND ART

Conventionally, in a production line for sanitary napkins and the like, for the purpose of integrating the continuous sheet 2a made of such as nonwoven fabric that becomes the top sheet 2 (the sheet that comes into contact with the wearer's skin when using the absorbent article 1) at the end product state, and the absorbent body 3 made of liquid absorbent fiber and the like, there is a process of sending through the space between the embossing roll 10b and the anvil roll 10a the continuous sheet 2a with the absorbent body 3 (corresponding to polymeric material) overlapping at the central portion in the width direction of the continuous sheet 2 (for example, refer to FIG. 2).

And when the continuous sheet 2a passes through the space between the rolls, the embossing protrusion 12 (corresponding to the protruding member) on the outer circumferential surface of the embossing roll 10b presses against the aforementioned central portion from the continuous sheet 2a side, and thereby a groove like depression 7 is formed at said central portion by pressing to integrate the absorbent body 3 with the continuous sheet 2a (PTL 1).

CITATION LIST

Patent Literature

[PTL 1] Japanese Patent Application Laid-open Publication No. 2000-14701

SUMMARY OF INVENTION

Technical Problem

However, there is a case where wrinkles 2f, along the direction of travel of the continuous sheet 2a, are made around the groove like depression 7 of the continuous sheet 2a resulting from pressing by the embossing protrusion 12 from this continuous sheet 2a side (for example, refer to FIG. 3). In other words, at the time of pressing, the area surrounding the groove like depression 7 of the continuous sheet 2a is drawn to the inside in the width direction to create wrinkles 2f. And when these wrinkles 2f remain in the end product, the appearance of the absorbent article 1 is spoiled and further, during the use of the absorbent article 1, there is possibility that body fluids, such as menses that should be absorbed, will run along these wrinkles 2f and leak out of the absorbent article 2f.

The present invention has been made in view of the above problem and an object thereof is to smooth out wrinkles of a composite body of a continuous sheet to which depressions are made by pressing with a protruding member while a polymeric material is overlapped on the continuous sheet at a central portion thereof.

Solution to Problem

In order to solve the above-described problem, a principal aspect of the invention is a device that smoothes out wrinkles of a composite body of a continuous sheet, in a state a polymeric material is overlapped to a central portion in a width direction of the continuous sheet that travels, to which a depression is shaped at the central portion by a protruding member being pressed against the central portion from the continuous sheet side, the wrinkle smoothing device for a composite body of a continuous sheet related to an absorbent article including a first belt that moves along a first travel path while retaining the central portion of the continuous sheet; a second belt that is provided adjacent the first belt on one side in the width direction thereof, and that moves along a second travel path while retaining a portion at the one side from the central portion of the continuous sheet; and a third belt that is provided adjacent the first belt on an other side in the width direction thereof, and that moves along a third travel path while retaining a portion at the other side from the central portion of the continuous sheet, wherein the second travel path is inclined from the first travel path such that a downstream side is more spaced apart from the first travel path to the one side in the width direction than the upstream side, the third travel path is inclined from the first travel path such that a downstream side is more spaced apart from the first travel path to the other side in the width direction than the upstream side, the second belt retains a portion on the one side of the continuous sheet while relatively sliding in the width direction of the continuous sheet, and the third belt retains a portion on the other side of the continuous sheet while relatively sliding in the width direction of the continuous sheet.

And a further aspect of the invention is a method of smoothing out wrinkles of a composite body of a continuous sheet, in a state a polymeric material is overlapped to a central portion in a width direction of the continuous sheet that travels, to which a depression is shaped at the central portion by a protruding member being pressed against the central portion from the continuous sheet side, the wrinkle smoothing method for a composite body of a continuous sheet related to an absorbent article including moving a first belt along a first travel path while making the first belt that is provided along the first travel path retain the central portion of the continuous sheet; moving a second belt along a second travel path while making the second belt that is provided adjacent the first belt on the one side in the width direction thereof retain a portion at one side from the central portion of the continuous sheet; and moving a third belt along a third travel path while making the third belt provided adjacent the first belt on the other side in the width direction thereof retain a portion at an other side from the central portion of the continuous sheet, and, wherein the second travel path is inclined from the first travel path such that a downstream side is more spaced apart from the first travel path to the one side in the width direction, than the upstream side the third travel path is inclined from the first travel path such that a downstream side is more spaced apart from the first travel path to the other side in the width direction than the upstream side, the second belt retains a portion on the one side of the continuous sheet while relatively sliding in the width direction of the continuous sheet, and the third belt retains a portion on the other side of the continuous sheet while relatively sliding in the width direction of the continuous sheet.

Features of the invention other than the above will become clear from the description of the present specification and the drawings attached.

Advantageous Effects of Invention

According to the present invention, it is possible to smooth out wrinkles of a composite body of a continuous sheet to which a depression is made by pressing with a protruding member while a polymeric material is overlapped on the continuous sheet at a central portion thereof. And as a result, wrinkles can be restrained from being made to this composite body.

BRIEF DESCRIPTION OF DRAWINGS

FIG. 3 is an underside view of partially-finished products 1a for explaining the wrinkles that may be made on top sheet 2a.

MODE FOR CARRYING OUT THE INVENTION

Figure 1A:
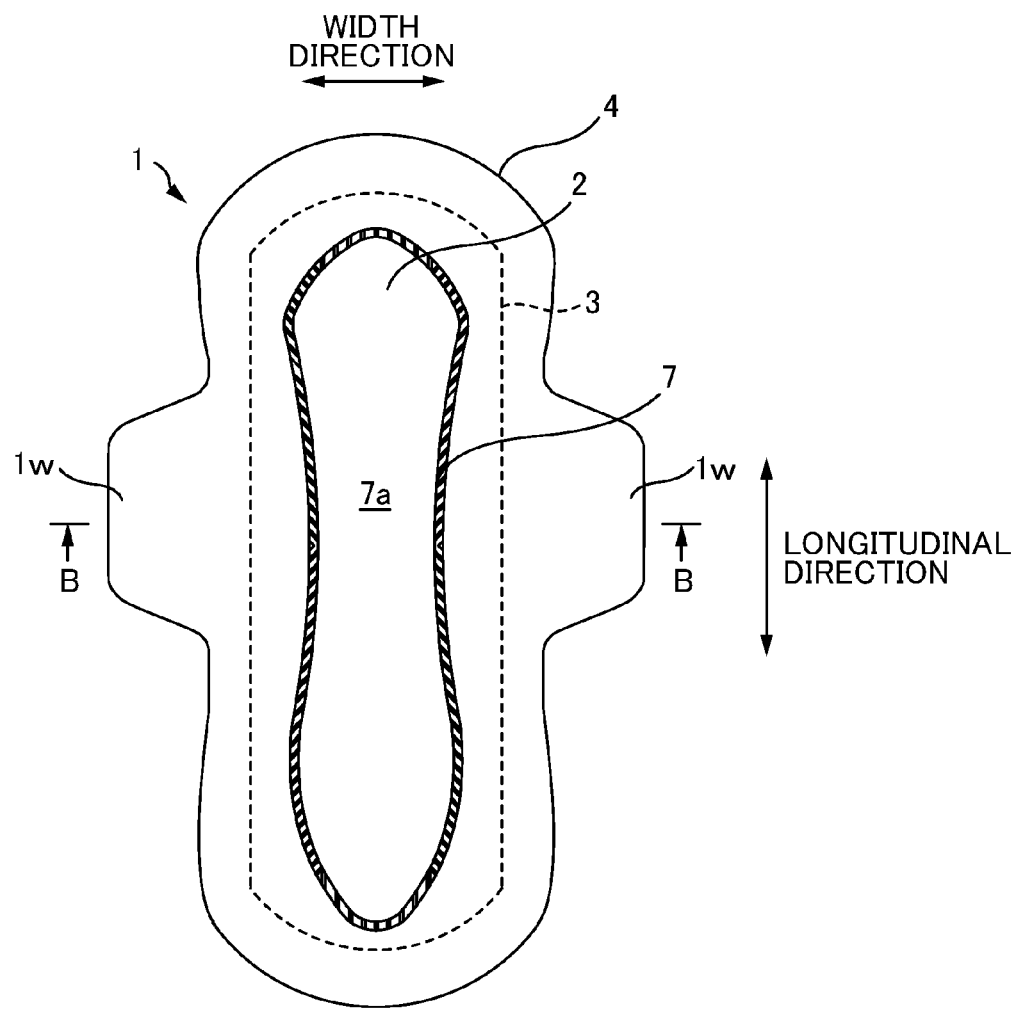
FIG. 1A is a plane view of napkin 1.

At least the following matters will be made clear from the description of the present specification with reference to the accompanying drawings.

First, the wrinkle smoothing device for a composite body of a continuous sheet related to an absorbent article according to the present invention is a device that smoothes out wrinkles of a composite body of a continuous sheet, in a state a polymeric material is overlapped to a central portion in a width direction of the continuous sheet that travels, to which a depression is shaped at the central portion by a protruding member being pressed against the central portion from the continuous sheet side, the wrinkle smoothing device for a composite body of a continuous sheet related to an absorbent article including a first belt that moves along a first travel path while retaining the central portion of the continuous sheet; a second belt that is provided adjacent the first belt on one side in the width direction thereof, and that moves along a second travel path while retaining a portion at the one side from the central portion of the continuous sheet; and a third belt that is provided adjacent the first belt on an other side in the width direction thereof, and that moves along a third travel path while retaining a portion at the other side from the central portion of the continuous sheet, wherein the second travel path is inclined from the first travel path such that a downstream side is more spaced apart from the first travel path to the one side in the width direction than the upstream side, the third travel path is inclined from the first travel path such that a downstream side is more spaced apart from the first travel path to the other side in the width direction than the upstream side, the second belt retains a portion on the one side of the continuous sheet while relatively sliding in the width direction of the continuous sheet, and the third belt retains a portion on the other side of the continuous sheet while relatively sliding in the width direction of the continuous sheet.

According to such a device that smoothes out wrinkles of a composite body of a continuous sheet for absorbent articles, the second travel path and the third travel path are each set so that the paths respectively incline such that the upstream side is distant from the first travel path, compared to the downstream side. Therefore, the second and the third belts moving along the corresponding travel paths while holding the end portions in the width direction of the continuous sheet, allows the continuous sheet to be pulled toward the outside in the width direction to smooth out the continuous sheet, and thereby the wrinkles, in the continuous sheet, along the travel direction can be surely smoothed.

Further, the second and third belts slide relative to the continuous sheet enabling to effectively restrain the continuous sheet from being damaged such as ripping by an excessive amount of tensile strength acting in the width direction.

It is preferable that in the wrinkle smoothing device for a composite body of a continuous sheet related to an absorbent article the first belt, the second belt, and the third belt each have an air inlet, the first belt retains the central portion by suction-adhering the central portion of the continuous sheet, the second belt retains the portion at the one side by suction-adhering the portion at the one side in the width direction of the continuous sheet, and the third belt retains the portion at the other side by suction-adhering the portion at the other side in the width direction of the continuous sheet.

According to such a device that smoothes out wrinkles of a composite body of a continuous sheet for absorbent articles, the first, second and third belts can respectively retain the parts to be retained of the continuous sheet by suction adhesion.

Further, a device above the first, second and third belts, and a separate retaining belt and the like need not be placed. Thus space above the first, second and third belts can be kept open allowing easy monitoring of the traveling state of the continuous sheet and easy recovery work to be carried out when troubles should occur.

It is preferable that in the wrinkle smoothing device for a composite body of a continuous sheet related to an absorbent article the continuous sheet is positioned to the first belt side from the polymeric material.

According to such a device that smoothes out wrinkles of a composite body of a continuous sheet for absorbent articles, the continuous sheet is situated on the first belt side than the polymeric material. In other words, the continuous sheet is situated between the polymeric material and the first belt. In this way, the second and third belts can smoothly pull the continuous sheet in said width direction without creating level difference of an amount equaling to the thickness of the polymeric material and as a result the device exhibits excellent wrinkle smoothing ability.

It is preferable that in the wrinkle smoothing device for a composite body of a continuous sheet related to an absorbent article the polymeric material is an absorbent body made by forming liquid absorbent fiber into a predetermined shape, the absorbent body is placed intermittently on the continuous sheet at a predetermined pitch along the first travel path, the continuous sheet is a sheet having air permeability and liquid permeability to cover the absorbent body, and the second belt and the third belt does not retain the absorbent body but retains only the continuous sheet.

According to such a device that smoothes out wrinkles of a composite body of a continuous sheet for absorbent articles, the airflow resistance of the first belt becomes larger than the second and third belts by an amount of the existence of the absorbent article and hereby is likely to increase the retaining force imparted on the continuous sheet. And thus allows to easily perform a setting of retaining the continuous sheet in a manner avoiding the continuous sheet from sliding relative to the first belt but allowing the continuous sheet to slide relative the second and third belts in the width direction of the continuous sheet.

It is preferable that in the wrinkle smoothing device for a composite body of a continuous sheet relating an absorbent article the first belt, the second belt and the third belt are moved in a manner such that a speed value for the first belt to move along the first travel path and a speed value for the second belt to move along the second travel path and a speed value for the third belt to move along the third travel path become equal with each other.

According to such a device that smoothes out wrinkles of a composite body of a continuous sheet related to absorbent articles, allows commonality of the drive mechanism for the first, second and third belts. In other words, when these three belts are wound around one drive roller, the first to third belts can be driven at one time and thereby the configuration of the device can be simplified.

Further, the method for smoothing out wrinkles of a composite body of a continuous sheet according to the present invention is a method of smoothing out wrinkles of a composite body of a continuous sheet, in a state a polymeric material is overlapped to a central portion in a width direction of the continuous sheet that travels, to which a depression is shaped at the central portion by a protruding member being pressed against the central portion from the continuous sheet side, the wrinkle smoothing method for a composite body of a continuous sheet related to an absorbent article including moving a first belt along a first travel path while making the first belt that is provided along the first travel path retain the central portion of the continuous sheet; moving a second belt along a second travel path while making the second belt that is provided adjacent the first belt on the one side in the width direction thereof retain a portion at one side from the central portion of the continuous sheet; and moving a third belt along a third travel path while making the third belt provided adjacent the first belt on the other side in the width direction thereof retain a portion at an other side from the central portion of the continuous sheet, and, wherein the second travel path is inclined from the first travel path such that a downstream side is more spaced apart from the first travel path to the one side in the width direction, than the upstream side the third travel path is inclined from the first travel path such that a downstream side is more spaced apart from the first travel path to the other side in the width direction than the upstream side, the second belt retains a portion on the one side of the continuous sheet while relatively sliding in the width direction of the continuous sheet, and the third belt retains a portion on the other side of the continuous sheet while relatively sliding in the width direction of the continuous sheet.

According such a method for smoothing out wrinkles of a composite body of a continuous sheet related to absorbent articles, the second travel path and the third travel path are each set so that the paths respectively incline such that the upstream side is distant from the first travel path, compared to the downstream side. Therefore, the second and the third belts moving along the corresponding travel paths while retaining the end portions in the width direction of the continuous sheet, allows the continuous sheet to be pulled toward the outside in the width direction to smooth out the continuous sheet, and thereby the wrinkles, in the continuous sheet, along the travel direction can be surely smoothed.

Further, the second and third belts slide relatively to the continuous sheet enabling to effectively restrain the continuous sheet from being damaged such as ripping by an excessive amount of tensile strength acting in the width direction.

The First Embodiment

The wrinkle smoothing device 30 according to the first embodiment is used in a manufacturing line for sanitary napkins 1 as one example of an absorbent article.

Figure 1B:
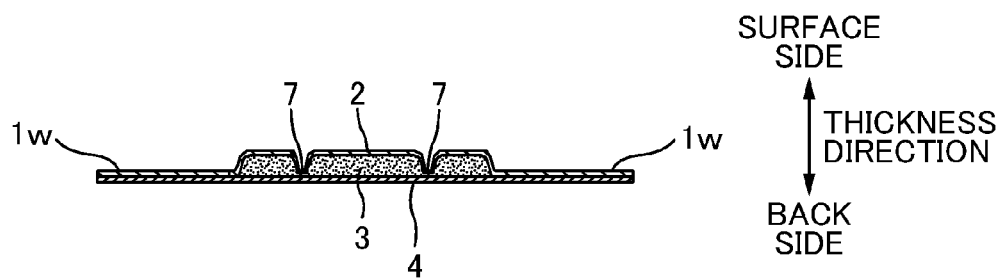
FIG. 1B is a sectional view taken along line B-B of FIG. 1A.

FIG. 1A is a plane view of napkin 1 and FIG. 1B is a sectional view taken along line B-B of FIG. 1A.

Napkin 1 includes, for example, top sheet 2 made of nonwoven fabric and the like having air permeability and liquid permeability, backsheet 4 that is liquid impermeable such as films and the like, and absorbent body 3 interposed between the top sheet 2 and the backsheet 4 to absorb body fluid.

The absorbent body 3 has a main body that is made of liquid absorbing fiber such as pulp fiber and the like, and formed into a predetermined shape such as an approximate rectangular parallelepiped. The planar size thereof is smaller than both the top sheet 2 and the backsheet 4 as to both the longitudinal direction and the width direction of the napkin 1. Therefore, the sheets 2, 4 are affixed together at the parts extending out from the absorbent body 3 as to the aforementioned two directions. And in this way, the absorbent body 3 is retained between the two sheets 2, 4.

Further, among the surfaces (which is the face that comes into contact with the skin and is also referred to as the skin side contact surface, hereafter) of the top sheet 2 being the face on the top sheet 2 side of the napkin 1, embossing groove 7 as an example of a depression is formed, at substantially the central portion in the longitudinal direction and the width direction, by pressing in the thickness direction of napkin 1 by embossing and the like. And thereby, the top sheet 2 and the absorbent body 3 are integrated into one piece. Further, this embossing groove 7 defines on the surface of top sheet 2a a closed area 7a of an approximate oblong shape lengthwise in the longitudinal direction of napkin 1 however, the shape is not limited to an approximate oblong shape and may be of any other shape, and furthermore a plurality of island shaped depressions can be collectively formed by pressing instead of the embossing groove 7.

Furthermore, napkin 1 has at an approximately central portion in the longitudinal direction thereof, a pair of wing portions 1w, 1w protruding outward in the width direction. Here, these wing portions 1w, 1w do not exist to the absorbent body 3 and the contour of these wing portions 1w, 1w are shaped by punching with a die-cutter and the like the part at the outer side from the absorbent body 3 where the top sheet 2 and the backsheet 4 are affixed together.

By the way, the above mentioned absorbent body 3 is not limited to a formed body that is simply made by shaping pulp fiber but those that are made by covering the formed body made with pulp fiber with tissue paper may be used or may be those that have mixed therein high-absorbent polymer. Additionally, although nonwoven fabric is used as the top sheet 2 in this example, it is not limited to such as long as the sheet 2 has appropriate air permeability and liquid permeability in the thickness direction thereof.

In the manufacturing line of such napkin 1, partially-finished products of napkins 1 are transported in a predetermined transport direction and at a predetermined transport speed by an appropriate transport mechanism. And during this transport, various processes such as bonding and/or adhesion, pressing, punching and the like to the various components are performed on the partially-finished products. And the partially-finished product sequentially changes its state each and every time to produce napkin 1 in the final state shown in FIG. 1A.

Note that as an example of the transport mechanism for transporting the partially-finished product, for example, a suction belt conveyor having a retaining function by sucking to the belt surface being the carrying face, or a transport roller and the like are used.

Figure 2:
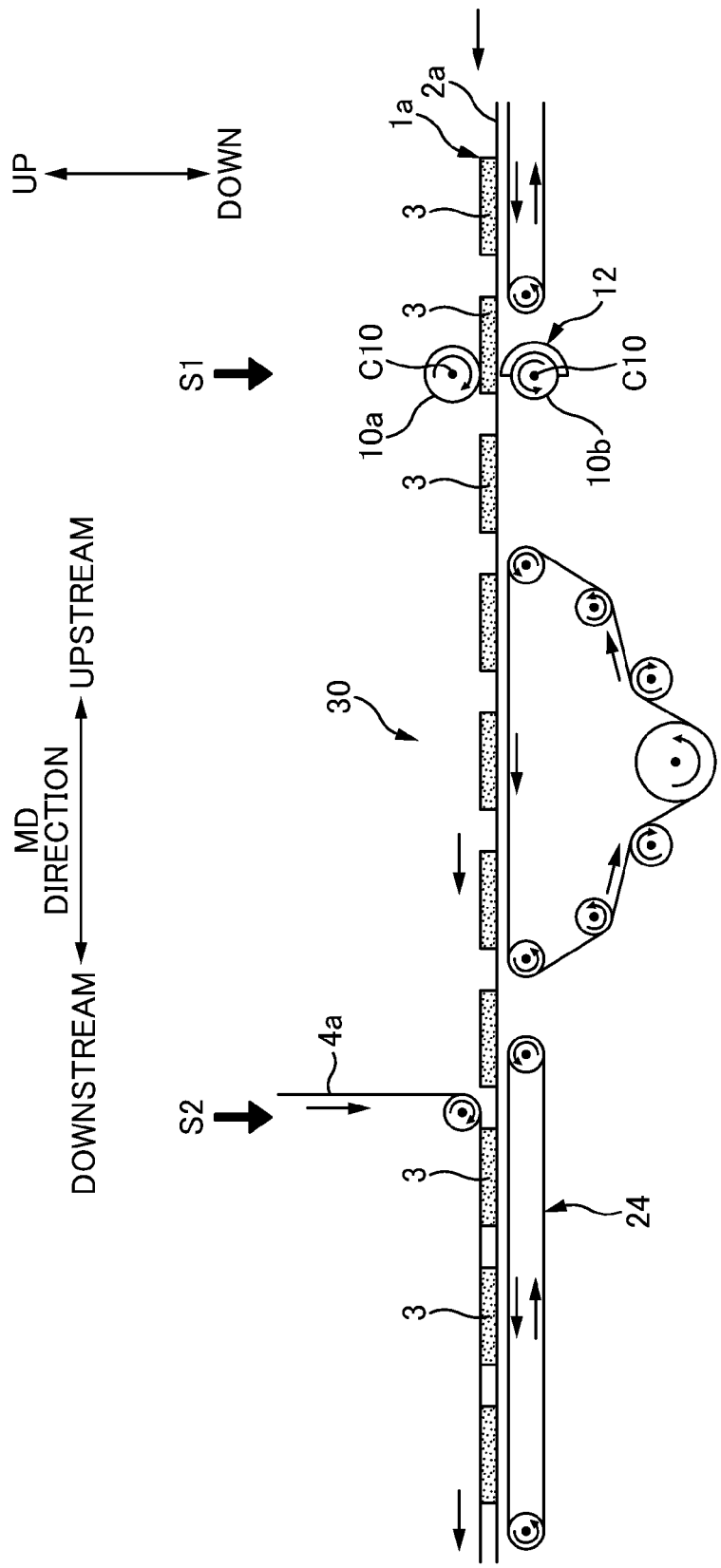
FIG. 2 is a schematic side view indicating sections S1 and S2 relating to the wrinkle smoothing device 30 in the napkin 1 manufacturing line.

FIG. 2 is a schematic side view showing sections S1 and S2, in closeup, relating to the wrinkle smoothing device 30 in the above described manufacturing line. Note that in the following description, the transport direction of the partially-finished product 1a is also referred to as the direction of travel or the MD direction, and the direction orthogonal to this transport direction (the direction perpendicular to the plane of the paper in FIG. 2) is referred to as the "CD direction" or the "right-left direction".

At section S1 shown in FIG. 2, partially-finished products 1a are, successively transported in the MD direction, in a state where a plurality of absorbent bodies 3, 3 . . . are placed on the upper surface of the continuous sheet 2a of top sheet 2 (hereinafter also referred to as simply top sheet 2). Specifically, the plurality of absorbent articles 3, 3 . . . (corresponding to polymeric material) are placed at the central portion in the CD direction of the surface of the same top sheet 2a, and at predetermined intervals in the MD direction.

Then at first, at the embossing work section S1, embossing grooves 7 are formed on the bottom from the underside corresponding to the surface (i.e., surface that comes into contact with the skin) of top sheet 2. In other words, at said section S1, there are placed a pair of top and bottom rolls 10a, 10b that are driven to rotate around the rotating shaft C10 extending in the CD direction while having their outer circumferential surfaces opposing each other. And in this example, the bottom roll 10b is the embossing roll that has the embossing protrusion 12 (corresponding to protruding member) on its outer circumferential surface and the top roll 10a is the anvil roll that receives the aforementioned embossing protrusion 12 on its smooth outer circumferential surface, so that embossing grooves 7 can be made from the top sheet 2 side and not the absorbent body 3 side. And the embossing protrusion 12, of an approximate oblong shape corresponding to the embossing groove 7, protrudes from the outer circumferential surface of the embossing roll 10b as shown in FIG. 1A described above. Therefore, when a partially-finished product 1a passes through the space between the rolls 10a, 10b, the central portion in the CD direction of said partially-finished product 1a is embossed by the embossing protrusion 12 to form by pressing the embossing groove 7 at the same central portion.

Then at section S2 downstream therefrom where the backsheet is adhered, as also shown in FIG. 2, a continuous sheet 4a of the backsheet 4 (hereinafter also referred to as simply backsheet 4a) is successively fed from above along the direction of transport of the partially-finished product 1a, and said backsheet 4a covers the partially-finished product 1a from above. Thereby, the backsheet 4a, while sandwiching the absorbent body 3 of the partially-finished product 1a between the top sheet 2a of the same partially-finished product 1a, is integrated with the top sheet 2a by adhesion. Then napkin 1 is formed further downstream by punching and the like into a planar shape shown in FIG. 1A by an appropriate rotary die cutter or the like, not shown.

Figure 3:
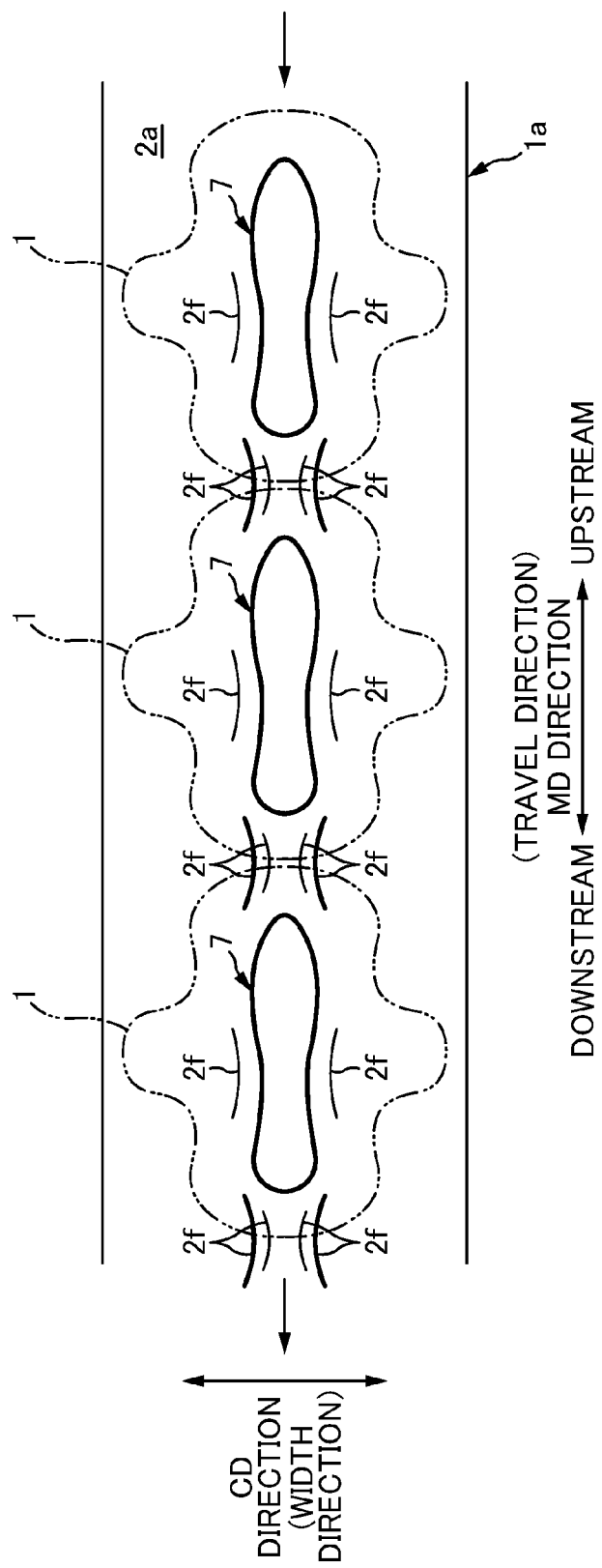

By the way, along with the processing of the above described embossing groove 7, wrinkles 2f develop in the area surrounding the embossing groove 7 in top sheet 2 as shown in the underside view of the partially-finished product 1a in FIG. 3. And these wrinkles 2f not only spoil the appearance of the napkin 1 but may become the cause for body fluids such as menses that should be absorbed during the use of the napkin 1 to leak out therefrom. In other words, there is a possibility that body fluids would run along these wrinkles 2f to reach the outer ridge and the like of the napkin 1 and leak outside.

For such reason, a wrinkle smoothing device 30 for smoothing out wrinkles 2f is placed between embossing section S1 and backsheet adhering section S2 as shown in FIG. 2. In the following, description will be given on this wrinkle smoothing device 30.

Figure 4A:
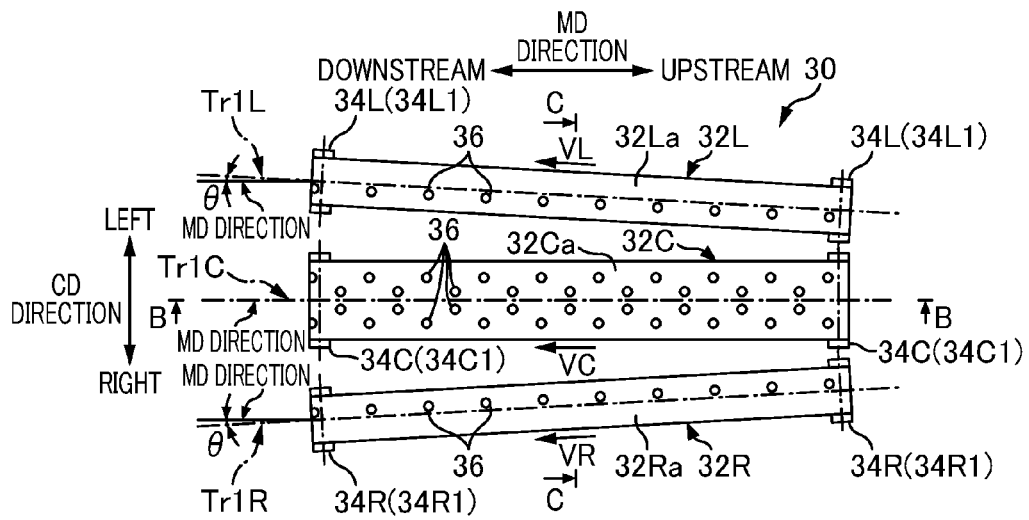
FIG. 4A is a schematic top view of the wrinkle smoothing device 30 according to the first embodiment.
Figure 4B:
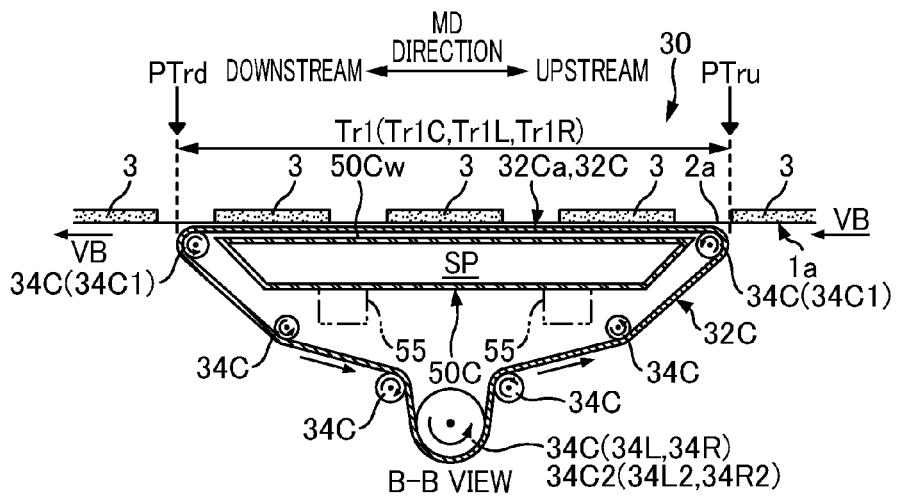
FIG. 4B is a diagram showing view B-B of FIG. 4A.
Figure 4C:
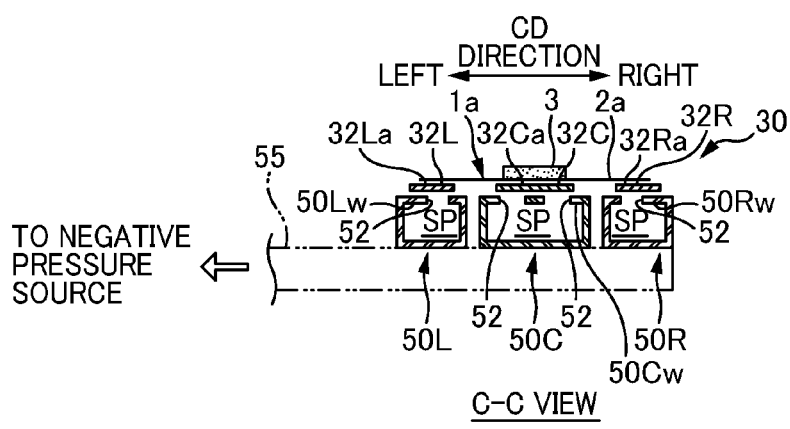
FIG. 4C is a diagram showing view C-C of FIG. 4B.

FIG. 4A to 4C shows schematic explanatory diagrams of the wrinkle smoothing device 30. FIG. 4A is a top view thereof, FIG. 4B shows view B-B of FIG. 4A and FIG. 4C shows view C-C of FIG. 4A. Note that the partially-finished product 1a is not shown in FIG. 4A in order to avoid confusion in the drawing.

Figure 5:
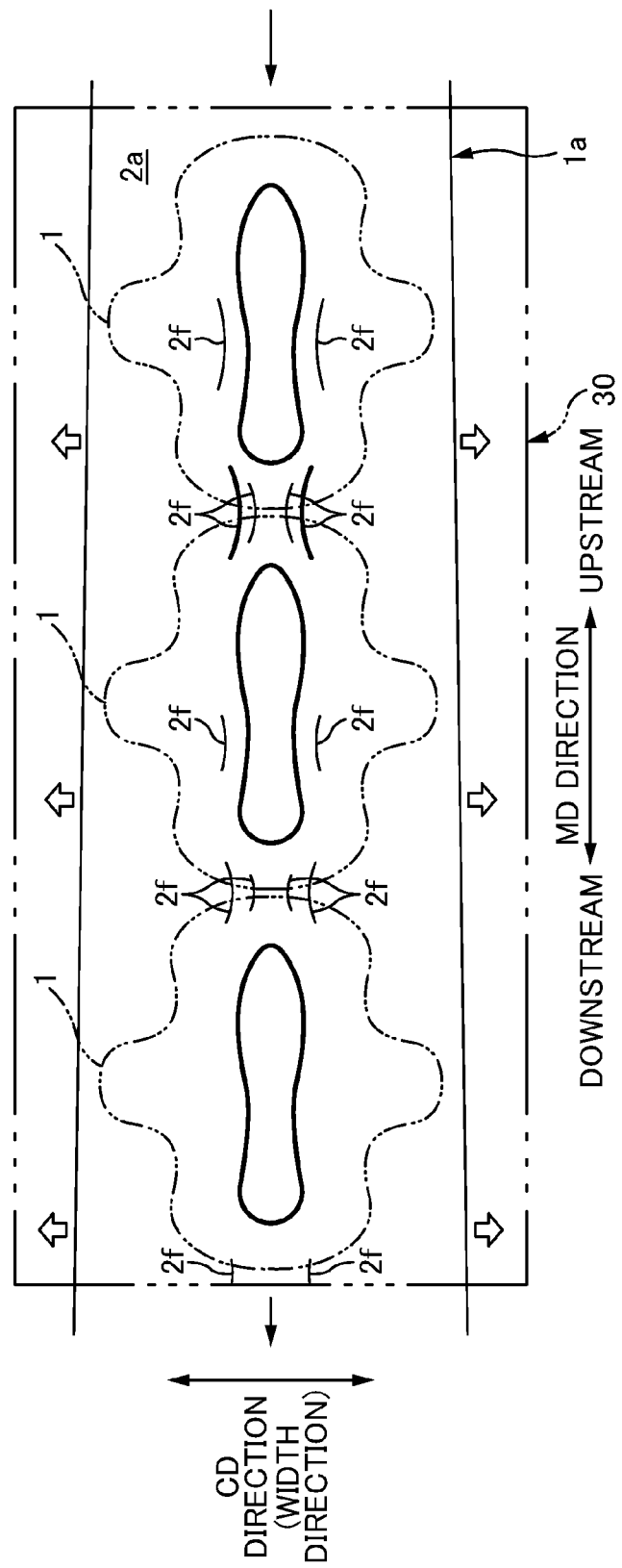
FIG. 5 is an underside view of partially-finished products 1a showing the way in which wrinkles 2f of the top sheet 2a are smoothed out by wrinkle smoothing device 30.

As shown in FIG. 2, the wrinkle smoothing device 30 is placed adjacent the embossing section S1 on the downstream side thereof. And with this wrinkle smoothing device 30, wrinkles 2f developed in the MD direction in the area surrounding the embossing groove 7 on the top sheet 2a of the partially-finished product 1a, are sequentially smoothed out as shown in the underside view of the partially-finished product 1a in FIG. 5. That is, while being transported by this wrinkle smoothing device 30 in the MD direction being the direction of transport, the areas of the top sheet 2a of the partially-finished product 1a (corresponding to the composite body of the continuous sheet) are gradually pulled to both sides in the CD direction being the width direction thereof as shown by hollow arrows in same FIG. 5. In this way wrinkles 2f in the MD direction are smoothed out little by little, and in the end at around the downstream end of the wrinkle smoothing device 30, reaches a state where there are approximately no wrinkles 2f. By the way, in FIG. 5, the contour of napkins 1 are shown in chain double-dashed imaginary lines for the ease of understanding the area where the wrinkles 2f are generated on napkins 1 however, such lines do not actually exist at this stage and this also holds true for the aforementioned FIG. 3.

The wrinkle smoothing device 30 with such function uses a suction belt conveyor for its main body for smoothing out wrinkles 2f of the top sheet 2a while transporting the partially-finished products 1a in the MD direction as explained above. In other words, as shown in FIGS. 4A to 4C, three continuous belts 32C, 32L, 32R whose belt surfaces 32Ca, 32La, 32Ra have retaining functions by suction, are placed side by side in the CD direction, and each of the belts 32C, 32L, 32R circle along respective circling paths situated in approximately the MD direction. And as shown in FIG. 4B, path Tr1 at the top horizontal portion of the circling path becomes the travel path Tr1 for the partially-finished product 1a. In other words, the belts 32C, 32L, 32R transport the partially-finished products 1a in the MD direction by retaining by suction (suction adhesion) top sheets 2a of the partially-finished products 1a with the belt surfaces 32Ca, 32La, 32Ra (outer circumferential surfaces of belts 32C, 32L, 32R, respectively) while travelling along the above horizontal path Tr1. And at the downstream end PTrd of this travel path Tr1, partially-finished products 1a are delivered and passed over to the transport mechanism 24 (FIG. 2) equipped to the aforementioned backsheet adhering section S2.

Here, a contrivance is made to the three belts 32C, 32L, 32R for smoothing out wrinkles 2f on the top sheet 2a of the partially-finished product 1a.

In the following, this contrivance will be explained however, in this explanation, the center belt 32C in the CD direction is referred to also as "center belt 32 (corresponding to the first belt)" and the aforementioned pair of belts 32L and 32R adjacently placed on the sides of the center belt 32C in the CD direction are referred to also as "left side belt 32L (corresponding to the second belt)" and "right side belt 32R (corresponding to the third belt)", respectively.

Further the above described travel path Tr1 of the center belt 32C is referred to also as the "center travel path Tr1C (corresponding to the first travel path)" and the above described travel path Tr1 of the left belt 32L is referred to also as the "left travel path Tr1L (corresponding to the second travel path)" and the above described travel path Tr1 of the right belt 32L is referred to also as the "right travel path Tr1R (corresponding to the third travel path)".

First, as shown in FIG. 4A, center travel path Tr1C of the center belt 32C is set in parallel with the MD direction. In contrast, the left travel path Tr1L of the left side belt 32L and the right travel path Tr1R of the right side belt 32R are respectively set to incline outward (opened) in the CD direction by a predetermined angle θ from the MD direction.

In other words, the left travel path Tr1L is inclined (opened) from the center travel path Tr1C such that the downstream side than the upstream side in the MD direction is spaced away to the left in the CD direction from the center travel path Tr1C, and the right travel path Tr1R is inclined (opened) from the center travel path Tr1C such that the downstream side than the upstream side in the MD direction is spaced away to the right in the CD direction from the center travel path Tr1C.

Therefore, according to such configuration, first the center belt 32C transports the partially-finished products 1a in the MD direction with its belt surface 32Ca retaining by suction (suction adhesion) the central parts, in the CD direction, of the top sheets 2a of the partially-finished products 1a. Additionally, concurrently therewith, the left side belt 32L and the right side belt 32R respectively circles while retaining by suction (suction adhesion) with belt surfaces 32La, 32Ra, the end portions, in the CD direction, of the top sheets 2a of the partially-finished products 1a however, at that time, the side belts 32L and 32R, with inclination angles of θ described above, pull the top sheet 2a toward the outside to the right and left in the CD direction to smooth out the top sheet 2a. And thereby, wrinkles 2f in the MD direction of the top sheets 2a are smoothed out.

At this time, the left side belt 32L and the right side belt 32R are set to relatively slide in the CD direction against the top sheet 2a while the end portions of the top sheet 2a are retained by suction. Therefore, the left side belt 32L and the right side belt 32R, based on the above described relative sliding, allows a degree of tensile strength, required to smooth out wrinkles 2f, to act on top sheet 2a without an excessive amount of tensile strength in the CD direction acting on the top sheet 2a. And as a result, damage such as ripping of the same sheet 2a can be effectively avoided. Note that, the setting method for retaining by suction of the ends of the top sheet 2a while causing relative sliding in the CD direction in such way will be described later.

By the way, the inclination angles θ, θ of the above-mentioned right-left side belts 32R, 32L are in mirror symmetry reflected along the MD direction, that is, the measure of the inclination angle θ is basically of the same value. However, there may be a case where the values may differ slightly. In other words, the inclination angles θ, θ are each arbitrarily selected from a range of, for example, 1-10 degrees. Here, the same value of four degrees is selected for the two inclination angles θ, θ.

Further, the value V of the circling speed of the belts 32C, 32L, 32R has basically the same speed value (m/sec) and in the present example, the three are set to have the same value. However, there may be a case where the two circling speed values VL, VR of the right-left side belts 32R, 32L are set differently with values within the range of ±5% of the circling speed value VC of the center belt 32C. And the circling speed value VC of the center belt 32C is, for example, controlled to approximately equal the travel speed value VB of the partially-finished products 1a at sections S1, S2 adjacent upstream and downstream the wrinkle smoothing device 30. In other words, the circling speeds VC, VL, VR of these belts 32C, 32L, 32R are synchronized with the above mentioned travel speed VB.

Here, much specific description on the configuration of this wrinkle smoothing device 30 will follow.

As shown in FIG. 4B, the belts 32C, 32L, 32R are wound around a plurality of rollers 34C, 34C . . . , 34L, 34L . . . , 34R, 34R . . . defining the circling path. In the example shown, there are seven rollers 34C, 34C . . . , 34L, 34L . . . , 34R, 34R . . . provided to the belts 32C, 32L, 32R, and the belts 32C, 32L, 32R are respectively wound around the corresponding ones of the seven rollers 34C, 34C . . . , 34L, 34L . . . , 34R, 34R . . . .

The rollers 34C, 34C . . . , 34L, 34L . . . , 34R, 34R . . . are each fixed at corresponding fixed positions prevented from moving, but rotatably supported to rotate around the axis of rotation along approximately the CD direction by a support member such as a frame not shown. And among these rollers 34C, 34C . . . , 34L, 34L . . . , 34R, 34R . . . , the pairs of rollers 34C1, 34C1, 34L1, 34L1, 34R1, 34R1 positioned at the very top, are the path line rollers that define the above mentioned travel paths Tr1C, Tr1L, Tr1R for the partially-finished products 1a.

In other words, in the example shown in FIG. 4A, corresponding to the center belt 32C, a pair of rollers 34C1, 34C1 are aligned in the MD direction with a predetermined space therebetween and thereby a horizontal center travel path Tr1C is set between theses two rollers 34C1, 34C1. And corresponding to the left side belt 32L, a pair of rollers 34L1, 34L1 are aligned in the MD direction with a predetermined space therebetween and thereby a horizontal left travel path Tr1L is set between these two rollers 34L1, 34L1. Further, corresponding to the right side belt 32R, a pair of rollers 34R1, 34R1 is aligned in the MD direction with a predetermined space therebetween and thereby a horizontal right travel path Tr1R is set between these two rollers 34R1, 34R1.

Figure 6:
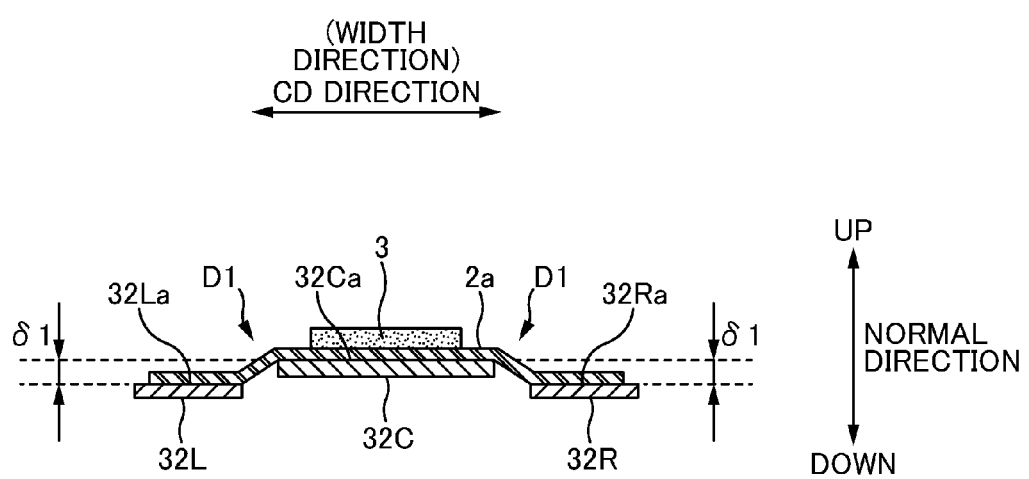
FIG. 6 is an explanatory diagram showing level difference D1 between belt surfaces 32Ca, 32La and 32Ra.

And in this example, these three travel paths Tr1C, Tr1L, Tr1R are all formed on the same plane. That is, as shown in FIG. 4C, the belt surfaces 32Ca, 32La, 32Ra of the three belts 32C, 32L, 32R are all positioned on the same plane at the above mentioned travel paths Tr1C, Tr1L, Tr1R. Therefore, the top sheet 2a can be retained in a stable manner by the belt surfaces 32Ca, 32La, 32Ra and at the same time, tensile force in the CD direction can be applied in a stable manner to the same sheet 2a. However, as shown in FIG. 6, a level difference D1 of some degree may be created between the belt surfaces 32Ca, 32La, 32Ra. In other words, the belt surfaces 32Ca, 32La, 32Ra while maintaining a state parallel with each other can be displaced of an amount within the range of 0 mm to 5 mm displacement amount δ1 in the direction normal to the belt surfaces 32Ca, 32La, 32Ra. But it is preferable that this displacement amount δ1 is small, since the stability to retain the top sheet 2a would decline when this displacement amount δ1 becomes large.

On the other hand, as shown in FIG. 4B, rollers 34C, 34L, 34R positioned at the very bottom are driving rollers 34C2, 34L2, 34R2 that are driven to rotate the belts 32C, 32L, 32R. Note that in this example, the driving rollers 34C2, 34L2, 34R2 of the belts 32C, 32L, 32R are combined, and are driven to rotate for example, by using a single electric motor as the drive source. Thereby, the three belts 32C, 32L, 32R circle while keeping the same circling speed of VC, VL, VR with each other. By the way, the driving rollers 34C2, 34L2, 34R2 here are only the rollers at the very bottom and the other rollers 34C, 34C . . . , 34L, 34L . . . , 34R, 34R . . . are so-called driven rollers. In other words, basically, these other rollers 34C, 34C . . . , 34L, 34L . . . , 34R, 34R . . . rotate along with the belts 32C, 32L, 32R, respectively, with which the outer circumferential surfaces thereof come into contact with.

Further, rollers 34C, 34L, 34R besides the above mentioned path line rollers 34C1, 34L1, 34R1 and the driving rollers 34C2, 34L2, 34R2, function as rollers for expanding the space inside the circling path for positioning the later described suction boxes 50C, 50L, 50R, or tension pulleys for winding the belts 32C, 32L, 32R around the driving rollers 34C2, 34L2, 34R2 at a predetermined winding angle.

By the way, the belts 32C, 32L, 32R were described to have a retaining function by suction to retain the top sheet 2a of the partially-finished product 1a to the belt surfaces 32Ca, 32La, 32Ra by suction, and this function is realized by such as the following configuration.

First, as shown in FIG. 4A, the belts 32C, 32L, 32R each have a plurality of similarly shaped penetration holes 36, 36 . . . (corresponding to intake holes) evenly distributed along the entire length of the belts 32C, 32L, 32R. Further, as shown in FIGS. 4B and 4C, suction boxes 50C, 50L, 50R of approximately rectangular parallelepiped box shapes are positioned in the space within the circling path of the belts 32C, 32L, 32R, and the inner spaces SP, SP, SP of the suction boxes 50C, 50L, 50R are maintained at negative pressure through the fluid communication with an appropriate negative pressure source. And among the walls provided to the suction boxes 50C, 50L, 50R, the top walls 50Cw, 50Lw, 50Rw opposing the aforementioned travel paths Tr1C, Tr1L, Tr1R, have a plurality of longholes 52, 52 . . . formed along the MD direction penetrated in the wall thickness direction and air of an amount appropriate for the aforementioned negative pressure state is drawn in through these longholes 52, 52 . . . (refer also to FIG. 7A accordingly).

Therefore, while the belts 32C, 32L, 32R travel, along the circling path, through the aforementioned travel paths Tr1C, Tr1L, Tr1R being paths opposing the top walls 50Cw, 50Lw, 50Rw, of the circling path, of the suction boxes 50C, 50L, 50R, air is drawn in through the penetration holes 36, 36 . . . of the belts 32C, 32L, 32R thereby retaining by suction partially-finished products 1a to the belt surfaces 32Ca, 32La, 32Ra. Whereas after the belts 32C, 32L, 32R finish travelling through the travel paths Tr1C, Tr1L, Tr1R to reach the downstream end PTrd of the travel paths Tr1C, Tr1L, Tr1R, air intake through the penetration holes 36, 36 . . . of the belts 32C, 32L, 32R are stopped, in other words retaining by suction is at a stopped state until the belts 32C, 32L, 32R pass through the location of the driving rollers 34C2, 34L2, 34R2 to return to the upstream end PTru of the travel path Tr1C, Tr1L, Tr1R.

Additionally, in the above description it was explained that the left side belt 32L and the right side belt 32R respectively slide relative to the top sheet 2a of the partially-finished product 1a in the CD direction at the aforementioned travel path Tr1 while retaining by suction however, such retaining by suction accompanying relative sliding is achieved by adjusting the retaining force relating to the retaining by suction.

For example, in the example shown in FIG. 4A, the retaining force for retaining by suction the partially-finished product 1a at the aforementioned travel path Tr1 is equally set for the left side belt 32L and the right side belt 32R. However, the retaining force FC (kN) of the center belt 32C is set larger than the sum value (=FL+FR) of the retaining force FL (kN) of the left side belt 32L and the retaining force FR (kN) of the right side belt 32R. And thereby, the center belt 32 C retains the top sheet 2a of the partially-finished product 1a with substantially no relative sliding therebetween however, the left side belt 32L and the right side belt 32R are made to retain the same sheet 2a while relatively sliding in the CD direction.

Figure 7A:
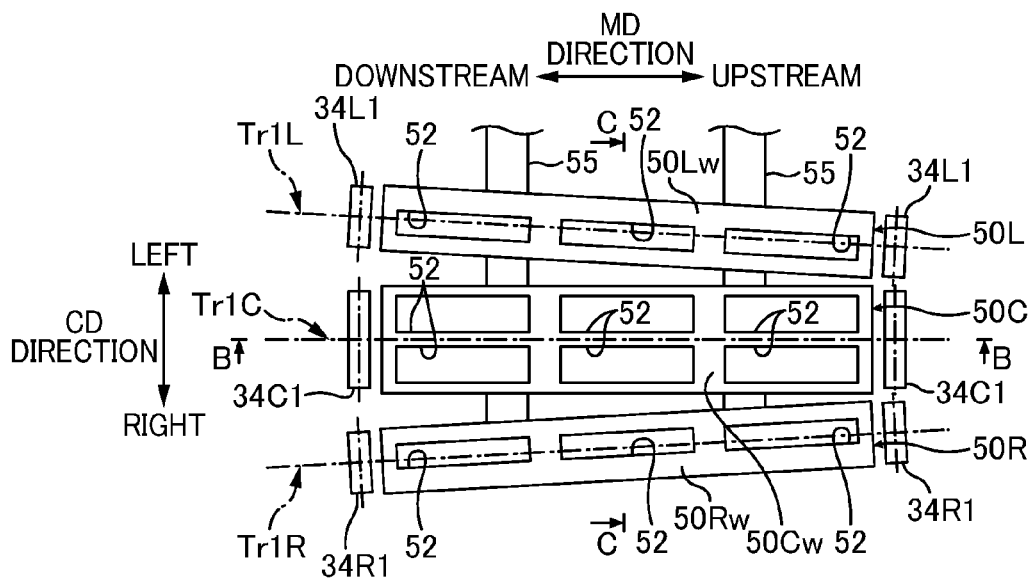
FIG. 7A is a schematic top view of suction boxes 50C, 50L and 50R.
Figure 7B:
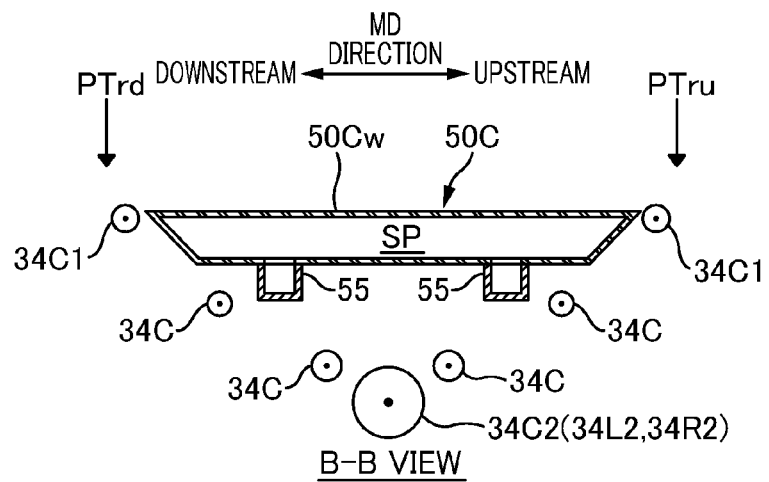
FIG. 7B is a diagram showing view B-B in FIG. 7A.
Figure 7C:
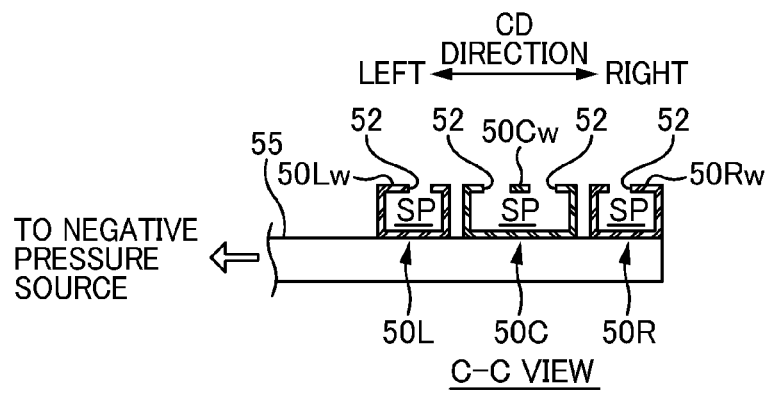
FIG. 7C is a diagram showing view C-C in FIG. 7A.

The adjustment of such retaining forces FC, FL, FR here are realized in the following manner. FIGS. 7A to 7C show schematic explanatory views of the suction boxes 50C, 50L, 50R. FIG. 7A is a top view thereof, FIG. 7B is a diagram showing view B-B in FIG. 7A and FIG. 7C is a diagram showing view C-C in FIG. 7A. Note that FIGS. 7A to 7C are diagrams corresponding to FIGS. 4A to 4C having belts 32C, 32L, 32R taken away.

First, the three suction boxes 50C, 50L, 50R are adjusted so that the negative pressures therein are of approximately the same value. For example as in the present example, an identical suction pipe 55 is directly connected to these three suction boxes 50C, 50L, 50R and thereby shares the suction pipe 55 that draws air from the suction boxes 50C, 50L, 50R and allows the pressure value of the three suction boxes 50C, 50L, 50R to be approximately the same. Note that as shown in FIGS. 7A and 7B, the suction pipes 55, 55 in this example are each positioned at a plurality of positions (two places in the example shown) in the MD direction and the suction pipes 55, 55 are connected to the aforementioned negative pressure source such as blowers and the like. And thereby, the air pressure inside the suction boxes 50C, 50L, 50R are made negative as described above.

And as shown in FIG. 4A, the total area of the penetration holes 36, 36 . . . located at the travel path Tr1 among the plurality of penetration holes 36, 36 . . . of the side belts 32L, 32R, are set such that those at the left side belt 32L and those at the right side belt 32R are the same. And at the same time, the total area of the penetration holes 36, 36 . . . located at the travel path Tr1 among the plurality of penetration holes 36, 36 . . . of the center belt 32C is set larger than the sum of the above total area with regard to the left side belt 32L and the above total area with regard to the right side belt 32R. In this way, the retaining force FC at the center belt 32C caused by air intake through the penetration holes 36, 36 is made larger than the total force (=FL+FR) of the retaining force FL of the left side belt 32L and the retaining force FR of the right side belt 32R.

By the way, as shown in FIG. 4C, since the airflow resistance becomes larger of an amount required by overlapping the absorbent body 3 at the central portion of the top sheet 2a to be retained by suction by the center belt 32C, the retaining force of the center belt 32C becomes larger of the same amount compared to the right and left side belts 32R, 32L. Therefore, it becomes more easier for these right and left side belts 32R, 32L to perform relative sliding which also effectively contributes to realizing the above mentioned retaining by suction while relatively sliding.

Further, in the example shown in this figure, the retaining forces FC, FL, FR were adjusted by setting the value of the total area of the penetration holes 36, 36 . . . of the belts 32C, 32L, 32R positioned at the travel path Tr1 however, the way of adjusting the forces is not limited to such. For example, in the case the suction boxes 50C, 50L, 50R are configured to allow individual adjustment of the air pressure values therein, the retaining forces FC, FL, FR may be adjusted by setting the air pressure values individually. As an example of an adjustment method in such case there is such as equalizing the negative air pressure values in the suction boxes 50R, 50L for the right and left side belts 32R, 32L, and reducing the negative air pressure value (i.e., raising the negative pressure level) in the suction box 50C for the center belt 32C to become lower than that for the aforementioned side belts 32R, 32L.

Preferably, the sizes of the longholes 52, 52 . . . of the suction boxes 50C, 50L, 50R in the CD direction are set to a size such that the penetration holes 36, 36 . . . that passes above the longholes 52, 52 . . . fit inside said longholes 52, 52 . . . . By doing so, the longholes 52, 52 . . . would not block any part of the penetration holes 36, 36 . . . in relation to the CD direction and can prevent blocking of air intake through the penetration holes 36, 36 . . . . Therefore, the sizes are set in such manner in the examples shown in FIGS. 4A and 7A.

Figure 8:
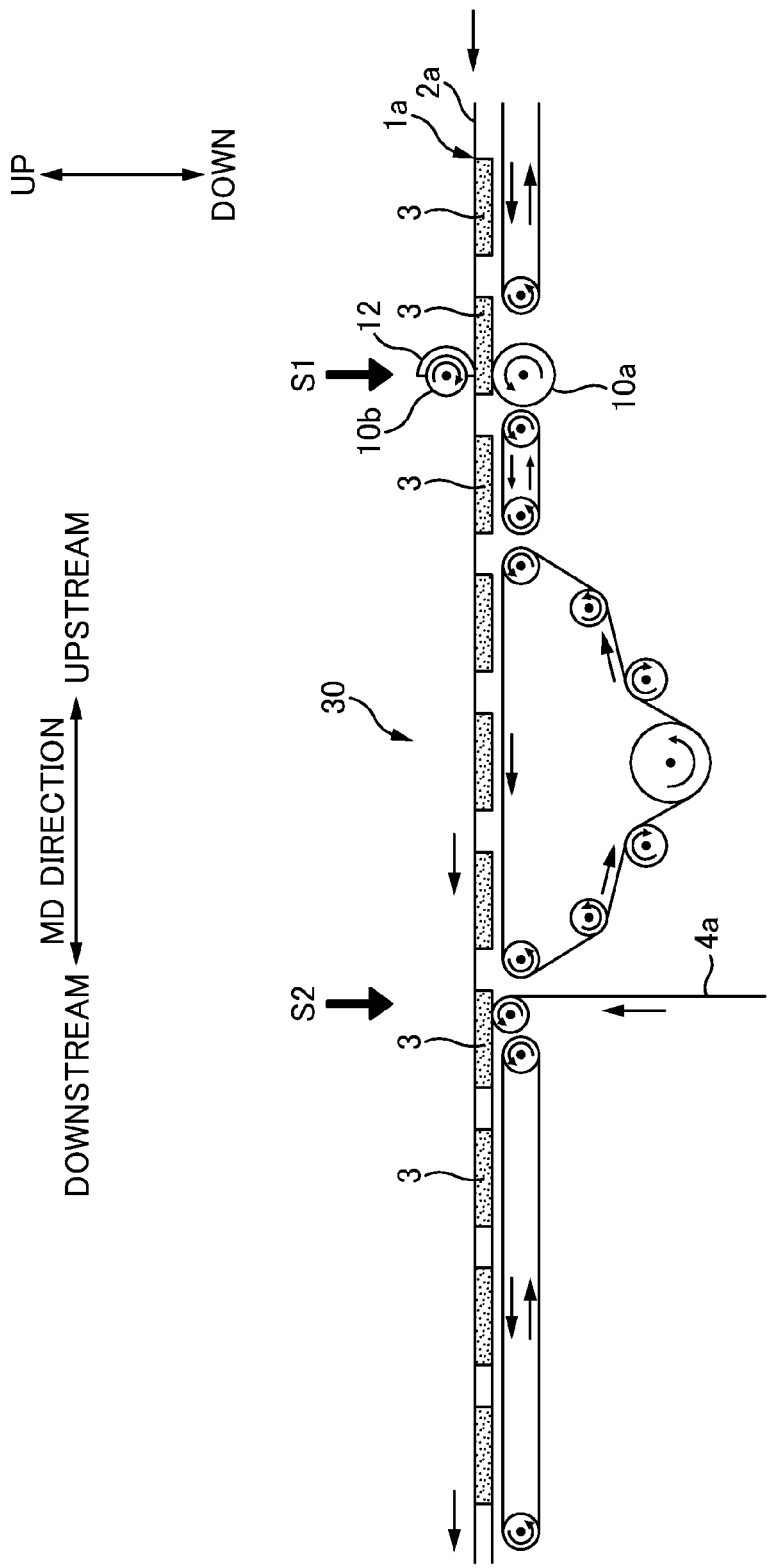
FIG. 8 is a schematic side view of a part of the production line showing that the top-bottom relationship of the partially-finished product 1a may be reversed.

By the way, in the above described first embodiment, the absorbent body 3 was overlapped on the surface of the top sheet 2a as shown in FIG. 2 however, the top-bottom relationship is not limited to such and the positional relationship may be reversed as shown in the schematic side view of FIG. 8. That is, the absorbent body 3 may be overlapped on the bottom side of the top sheet 2a.

And in this case, the top-bottom positional relationship of the embossing roll 10b and the anvil roll 10a of the embossing work section S1 will also be reversed, in other words, the anvil roll 10a will be positioned under the embossing roll 10b. Further, at the backsheet adhering section S2 the backsheet 4a will be provided from under the partially-finished products 1a and adhered thereto.

Figure 9:
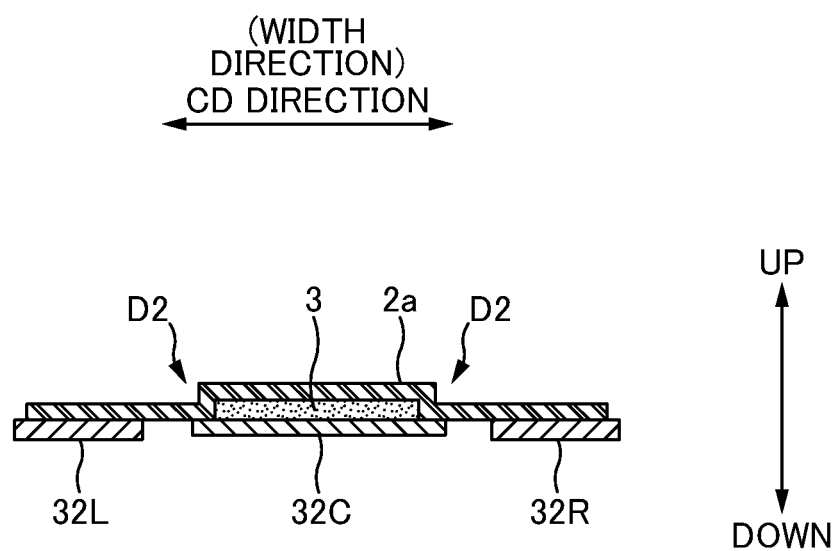
FIG. 9 is a diagram explaining the reason why the wrinkle smoothing ability is inferior in the case the top-bottom relationship of the partially-finished product 1a is reversed.

However, with regard to the wrinkle smoothing device 30, that with an absolutely same configuration as the one for the above described first embodiment can be applied. In other words, the wrinkle smoothing device 30 is used without the top-bottom relation being reversed. But in this case, the absorbent body 3 is positioned to the center belt 32C side than the top sheet 2a, therefore at locations between the center belt 32C and the right and left side belts 32R, 32L, a level difference D2 of an amount equaling to the thickness of the absorbent body 3 will be created and due to this, it would be difficult to apply in a smooth manner tensile force in the CD direction by the right and left side belts 32R, 32L, thus the top sheet 2a is regarded to have inferior smoothing ability as shown in FIG. 9. For such reason, from the viewpoint of smoothing ability, the configuration of the aforementioned first embodiment shown in FIG. 2 is preferred compared to the example shown in FIG. 8.

The Second Embodiment

Figure 10A:
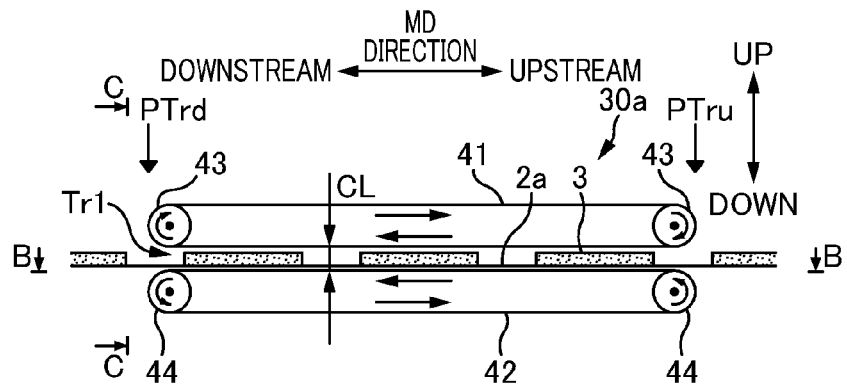
FIG. 10A is a schematic vertical sectional view seen through the center of the main part of the wrinkle smoothing device 30a according to the second embodiment.
Figure 10B:
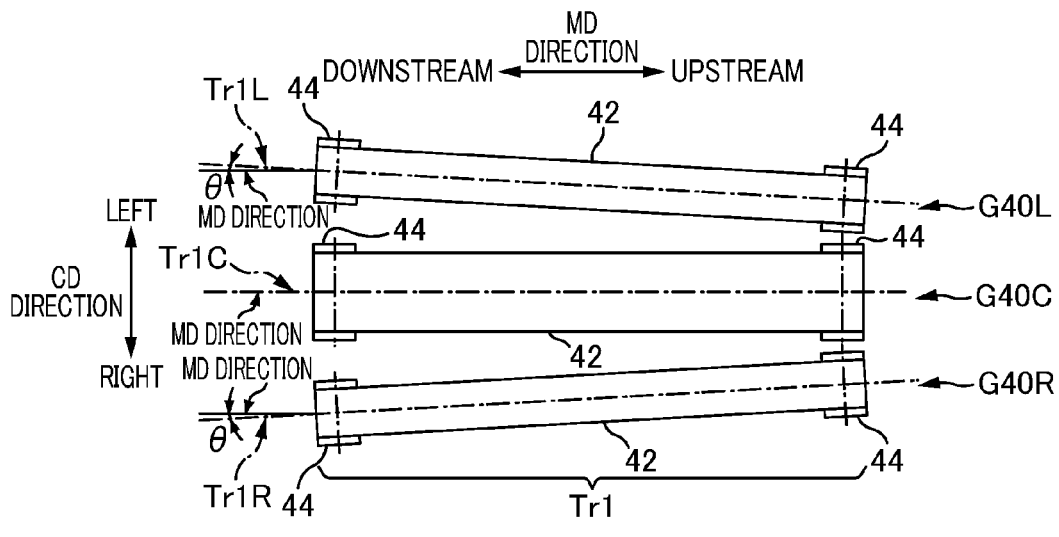
FIG. 10B is a diagram showing view B-B in FIG. 10A.
Figure 10C:
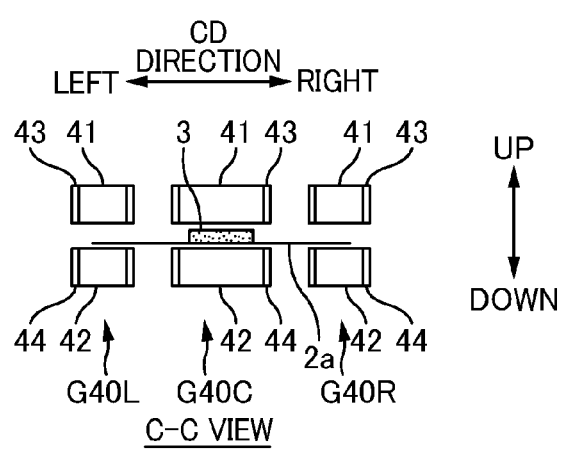
FIG. 10C is a diagram showing view C-C in FIG. 10A.

FIGS. 10A to 10C are schematic explanatory diagrams of the wrinkle smoothing device 30a according to the second embodiment. FIG. 10A is a schematic vertical sectional view seen through the center of the wrinkle smoothing device 30a. FIG. 10B is a diagram showing view B-B in FIG. 10A. FIG. 10C is a diagram showing view C-C in FIG. 10A. Note that, the partially-finished product 1a is not shown in FIG. 10B to avoid confusion in the drawing.

In the above-described first embodiment, retaining forces FC, FL, FR for retaining the partially-finished product 1a were realized by air intake from the penetration holes 36 in the belts 32C, 32L, 32R. However, this second embodiment differs on the point that compression force generated by sandwiching the partially-finished product 1a between the pair of top and bottom belts 41, 42 is used as the retaining force.

In other words, as shown in FIGS. 10A to 10C, this wrinkle smoothing device 30a has three sets of belt pairs G40C, G40L, G40R including a pair of top and bottom continuous belts 41, 42 arranged side by side in the CD direction. And the belt pairs G40C, G40L, G40R include a top continuous belt 41 circling along a predetermined circling path, and a bottom continuous belt 42, positioned under and opposing the top continuous belt 41, and circling along a predetermined circling path.

Note that in the following description, the belt pair G40C positioned at the center in the CD direction is referred to as also the "center belt pair G40C" and the right and left belt pairs G40R, G40L positioned adjacent to the center belt pair G40C and at the sides thereof in the CD direction are respectively referred to as also the "right side belt pair G40R" and the "left side belt pair G40L".

Further, since the basic structures of these belt pairs G40C, G40L, G40R are substantially the same, explanation on the belt pairs G40C, G40L, G40R will be given hereunder without distinguishing them. However, actually, the specifications of the devices slightly differ. For example, the width dimension of the continuous belts 41, 42 of the center belt pair G40C is wider than the width dimension of the continuous belts 41, 42 of the right and left side belt pairs G40R, G40L.

As shown in FIGS. 10A to 10C, the continuous belt 42 of the belt pairs G40C, G40L, G40R are respectively wound around a pair of rollers 44, 44 aligned in the MD direction with space therebetween. And at least one roller 44 among these rollers 44, 44 is driven to rotate by imparting rotational driving force from an electric motor (not shown) as a driving source and thereby circling the bottom continuous belt 42.

Meanwhile, the top continuous belts 41 of the belt pairs G40C, G40L, G40R are also wound around a pair of rollers 43, 43 aligned in the MD direction with space therebetween. And the top continuous belt 41 sandwiches the partially-finished products 1*a* with the opposing bottom endless belt 42 with a predetermined compression force to transport the partially-finished product 1*a*. In other words, with regard to each of the belt pairs G40C, G40L, G40R, the partially-finished products 1*a* are transported in an approximately integrated state with the continuous belts 41, 42 along the travel paths Tr1C, Tr1L, Tr1R each formed between the top continuous belt 41 and the bottom continuous belt 42. Thereafter, at its downstream end PTrd, the partially-finished product 1*a* is passed over to the transport mechanism 24 (FIG. 2) of the backsheet adhering section S2.

Note that, the top continuous belt 41 can be configured as a driven belt that is driven to circle by a drive force by the bottom continuous belt 42, or can be configured as a driving belt that is driven to circle by a drive force transmitted by the aforementioned electric motor and through an appropriate gear transmission mechanism and the like. It is a matter of course that in the latter case of circling by driving, the top continuous belt 41 synchronizes with the bottom continuous belt 42 while in a circling motion at the same circling speed.

By the way, as shown in FIGS. 10A and 10B, the travel path Tr1C (hereinafter referred to also as the center travel path Tr1C) formed between the top continuous belt 41 and the bottom continuous belt 42 at the center belt pair G40C, is set parallel with the MD direction. Meanwhile, the travel path Tr1L (hereinafter referred to also as the left travel path Tr1L) formed between the top continuous belt 41 and the bottom continuous belt 42 at the left side belt pair G40L, and the travel path Tr1R (hereinafter referred to also as the right travel path Tr1R) formed between the top continuous belt 41 and the bottom continuous belt 42 at the right side belt pair G40R are respectively set to incline outward (opened) in the CD direction by a predetermined angle θ from the MD direction (refer to FIG. 10B).

In other words, the left travel path Tr1L is inclined (opened) from the center travel path Tr1C such that the downstream side than the upstream side in the MD direction is spaced away to the left in the CD direction from the center travel path Tr1C, and the right travel path Tr1R is inclined (opened) from the center travel path Tr1C such that the downstream side than the upstream side in the MD direction is spaced away to the right in the CD direction from the center travel path Tr1C.

Therefore, according to such configuration, first the center belt pair G40C circles while retaining by compression force the central portion in the CD direction of the partially-finished product 1*a* to transport the partially-finished product 1*a*, at the aforementioned central travel path Tr1C. Additionally, concurrently therewith, the left side belt pair G40L and the right side belt pair G40R respectively circles while retaining by compression force the corresponding end portions in the CD direction of the top sheet 2*a* of the partially-finished product 1*a*, at the left travel path Tr1L and the right travel Tr1R however, at that time, the side belt pairs G40L, G40R, with inclination angles of θ described above, pull the top sheet 2*a* toward the outside in the CD direction to smooth out the top sheet 2*a*. And as a result, wrinkles 2*f* in the MD direction of the top sheets 2*a* are smoothed out into a state with substantially no wrinkles 2*f*.

At this time, the belts 41, 42 of the left side belt pair G40L and the belts 41, 42 of the right side belt pair G40R are set to relatively slide in the CD direction to the top sheet 2*a* while retaining by compression force the end portions of the top sheet 2*a*. Therefore, the left side belt pair G40L and the right side belt pair G40R, based on the above described relative sliding, allows a degree of tensile strength, required to smooth out wrinkles 2*f*, to act on top sheet 2*a* without an excessive amount of tensile strength in the width direction acting on the top sheet 2*a*. And as a result, damage such as ripping of the same sheet 2*a* can be effectively avoided.

Such retaining by compression force while relative sliding is, for example, realized by setting the amount of compression force for sandwiching the partially-finished product 1*a* with the top continuous belt 41 and the bottom continuous belt 42.

For example, the amount of compression force for retaining by sandwiching the partially-finished product 1*a* at the aforementioned travel paths Tr1L, Tr1R can be set to be the same for both the left side belt pair G40L and the right side belt pair G40R, and at the same time the amount of compression force FC (kN) of the center belt pair G40C of the travel path Tr1C can be set larger than the sum value (=FL+FR) of the compression force FL (kN) of the left side belt pair G40L of the travel path Tr1L and the compression force FR (kN) of the right side belt pair G40R of the travel path Tr1R.

Thereby, the center belt pair G40C retains by compression the partially-finished product 1*a* with substantially no relative sliding with the partially-finished product 1*a* however, the left side belt pair G40L and the right side belt pair G40R can retain by compression the top sheet 2*a* of the partially-finished product 1*a* while relatively sliding in the CD direction.

By the way, the adjustment of the compression forces FC, FL, FR described above can be performed, for example, by setting the clearance CL between the top continuous belt 41 and the bottom continuous belt 42 at the travel paths Tr1C, Tr1L, Tr1R, or by setting width dimensions of the top continuous belt 41 and the bottom continuous belt 42.

Further, the aforementioned inclination angles θ of the left side belt pair G40L and the right side belt pair G40R and the specification of the devices such as the circling speed of the belts 41, 42 are substantially the same as the aforementioned first embodiment therefore explanation thereof will be omitted.

Other Embodiments

Hereinabove, explanation on the embodiments of the present invention have been given however, the present invention is not limited to such embodiments and modification such as those in the following can be made.

In the aforementioned embodiment, an example was described of a case where the absorbent article 1 was a sanitary napkin 1 that absorbs menses as body fluid. However, the absorbent article 1 is not limited to such. The absorbent article 1 can be, for example, disposable diapers that absorb urine as body fluid (including excretory fluid), pet waste pads that absorb liquid excretion of pets, and the like.

In the aforementioned embodiment, absorbent body 3 made of liquid absorbent fiber and the like was exemplified as an example of polymeric material overlapped on the continuous sheet 2*a* however, the polymeric material is not limited to such. For example, a separate continuous sheet as polymeric material can be overlapped on the aforementioned continuous sheet 2a.

In the aforementioned embodiment, top sheet 2a made of air permeable nonwoven fabric was exemplified as the continuous sheet 2a however, the continuous sheet 2a is not limited to such. The continuous sheet 2a may be the backsheet, the continuous sheet 2a may be of film or woven fabric, or the continuous sheet 2a may be an impermeable sheet.

In the aforementioned embodiment, the travel paths Tr1C, Tr1L, Tr1R were set in the horizontal direction however, the direction is not limited to such. The travel paths Tr1C, Tr1L, Tr1R may be inclined at a predetermined angle from the horizontal direction.

In the aforementioned first embodiment, a wrinkle smoothing device 30 was exemplified in the case where the number of belts 32C, 32L, 32R equipped thereto was three. However, the number of belts is not limited to such and may be four or more. For example, one center belt 32C can be placed at the center with two of the left side belts 32L and right side belts 32R, each at both sides thereof. Similarly, in the second embodiment, a wrinkle smoothing device 30a was exemplified in the case where the number of pairs of the belt pairs G40C, G40L, G40R was three. However, the number of the belt pairs is not limited to such and may be four or more.

In the aforementioned first embodiment, the penetration holes 36, 36 . . . of the belts 32C, 32L, 32R were of perfect circles as shown in FIG. 4A however, the planar shape of the penetration holes 36 is not limited to perfect circles and may be for example, circular such as an oblong circle or of a polygonal shape such as a quadrangle.

In the aforementioned first embodiment, the longholes 52, 52 . . . of the suction boxes 50C, 50L, 50R were substantially rectangular long holes as shown in FIG. 7A. However, the shape is not limited to such and may be, for example, polygonal shapes besides a rectangle or circular shapes such as an oblong circle.

REFERENCE SIGNS LIST 1 sanitary napkin (absorbent article),
1a partially-finished product (composite body of continuous sheet), 1w wing portion,
2 top sheet, 2a top sheet (continuous sheet), 2f wrinkles,
3 absorbent body (polymeric material),
4 backsheet, 4a backsheet,
7 embossing groove (depression), 7a closed area,
10a anvil roll, 10b embossing roll,
12 embossing protrusion (protruding member),
24 transport mechanism,
30 wrinkle smoothing device, 30a wrinkle smoothing device
32C center belt (first belt), 32Ca belt surface,
32L left side belt (second belt), 32La belt surface,
32R right side belt (third belt), 32Ra belt surface,
34C roller,
34C1 path line roller,
34L1 path line roller,
34R1 path line roller,
34C2 driving roller, 34L2 driving roller, 34R2 driving roller,
36 penetration hole (air inlet),
41 top continuous belt, 42 bottom continuous belt,
43 roller, 44 roller,
50C suction box, 50Cw top wall,
50L suction box, 50Lw top wall,
50R suction box, 50Rw top wall,
52 longhole,
55 suction pipe,
G40C center belt pair,
G40L left side belt pair,
G40R right side belt pair,
S1 embossing work section, S2 backsheet adhering section,
Tr1 travel path,
Tr1C center travel path, Tr1L left travel path,
Tr1R right travel path,
PTrd downstream end, PTru upstream end,
SP inner space, C10 rotating shaft,
CL clearance, D1 level difference, D2 level difference

The invention claimed is:

1. A method of smoothing out wrinkles of a composite body of a continuous sheet for an absorbent article when the continuous sheet travels in a machine direction, in a state where a polymeric material overlaps a central portion of the continuous sheet in a cross machine direction crossing the machine direction and a depression is shaped at the central portion by a protruding member pressing against the central portion from a side of the continuous sheet, the wrinkle smoothing method comprising:
    moving a first belt along a first travel path while retaining the central portion of the continuous sheet by the first belt;
    moving a second belt along a second travel path while retaining a first side portion of the continuous sheet on a first side of the first belt from the central portion of the continuous sheet in the cross machine direction by the second belt provided adjacent to the first belt on the first side of the first belt in the cross machine direction crossing the machine direction; and
    moving a third belt along a third travel path while retaining a second side portion of the continuous sheet on a second side of the first belt from the central portion of the continuous sheet in the cross machine direction by the third belt provided adjacent to the first belt on the second side of the first belt in the cross machine direction, the second side opposite the first side in the cross machine direction
wherein
    the second travel path is inclined from the first travel path such that a downstream side of the second travel path is more spaced apart from the first travel path to the first side in the cross machine direction than the upstream side of the second travel path,
    the third travel path is inclined from the first travel path such that a downstream side of the third travel path is more spaced apart from the first travel path to the second side in the cross machine direction than an upstream side of the third travel path,
    the second belt retains the first side portion of the continuous sheet in a manner allowing the first side portion of the continuous sheet to slide relative to the second belt in the cross machine direction of the continuous sheet,
    the third belt retains the second side portion of the continuous sheet in a manner allowing the second side portion of the continuous sheet to slide relative to the third belt in the cross machine direction of the continuous sheet,
    the polymeric material forms absorbent bodies having liquid absorbent fibers,
    the continuous sheet has air permeability and liquid permeability and covers the absorbent bodies,
    the first belt retains the absorbent bodies placed intermittently on the continuous sheet at a predetermined pitch along the first travel path in a manner preventing the central portion of the continuous sheet from sliding relative to the first belt, and the second belt and the third belt retain the continuous sheet and do not retain the absorbent bodies.

2. The method according to claim 1, wherein the second belt and the third belt retain the continuous sheet and without directly contacting the absorbent bodies.

3. The method according to claim 1, wherein the first belt, the second belt, and the third belt each have an air inlet, the first belt retains the central portion by suction-adhering the central portion of the continuous sheet, the second belt retains the first side portion of the continuous sheet by suction-adhering the first side portion of the continuous sheet, and the third belt retains the second side portion of the continuous sheet by suction-adhering the second side portion of the continuous sheet.

4. The method according to claim 1, wherein the first belt supports the continuous sheet from a side opposite to the polymeric material.

5. The method according to claim 1, wherein the first belt, the second belt, and the third belt each have a plurality of air inlets, the second belt has an upstream half closer to the first belt in the cross machine direction than a downstream half of the second belt, the third belt has an upstream half closer to the first belt than a downstream half of the third belt in the cross machine direction, the plurality of air inlets of the second belt at the upstream half is closer to the first belt than the plurality of air inlets of the second belt at the downstream half further from the first belt, and the plurality of air inlets of the third belt at the upstream half is closer to the first belt than the plurality of air inlets of the third belt at the downstream half further from the first belt.

6. The method according to claim 5, wherein a total area of the plurality of air inlets of the first belt is larger than a sum of (i) a total area of the plurality of air inlets of the second belt and (ii) a total area of the plurality of air inlets of the third belt.

7. The method according to claim 6, wherein a retaining force of the first belt to retain the continuous sheet and the absorbent bodies at the first travel path is larger than a sum of (i) a retaining force of the second belt to retain the continuous sheet and (ii) a retaining force of the third belt to retain the continuous sheet, such that the second and third belts slide relative to the continuous sheet in the cross machine direction and the first belt does not slide relative to the continuous sheet in the cross machine direction.

8. The method according to claim 1, wherein the first belt, the second belt, and the third belt each are wound around a plurality of rollers defining corresponding circling paths including the first travel path of the first belt, the second travel path of the second belt, and the third travel path of the third belt.

* * * * *